June 22, 1937. E. H. SCHULTZ Plant Pat. 252
PHLOX
Filed Dec. 11, 1936
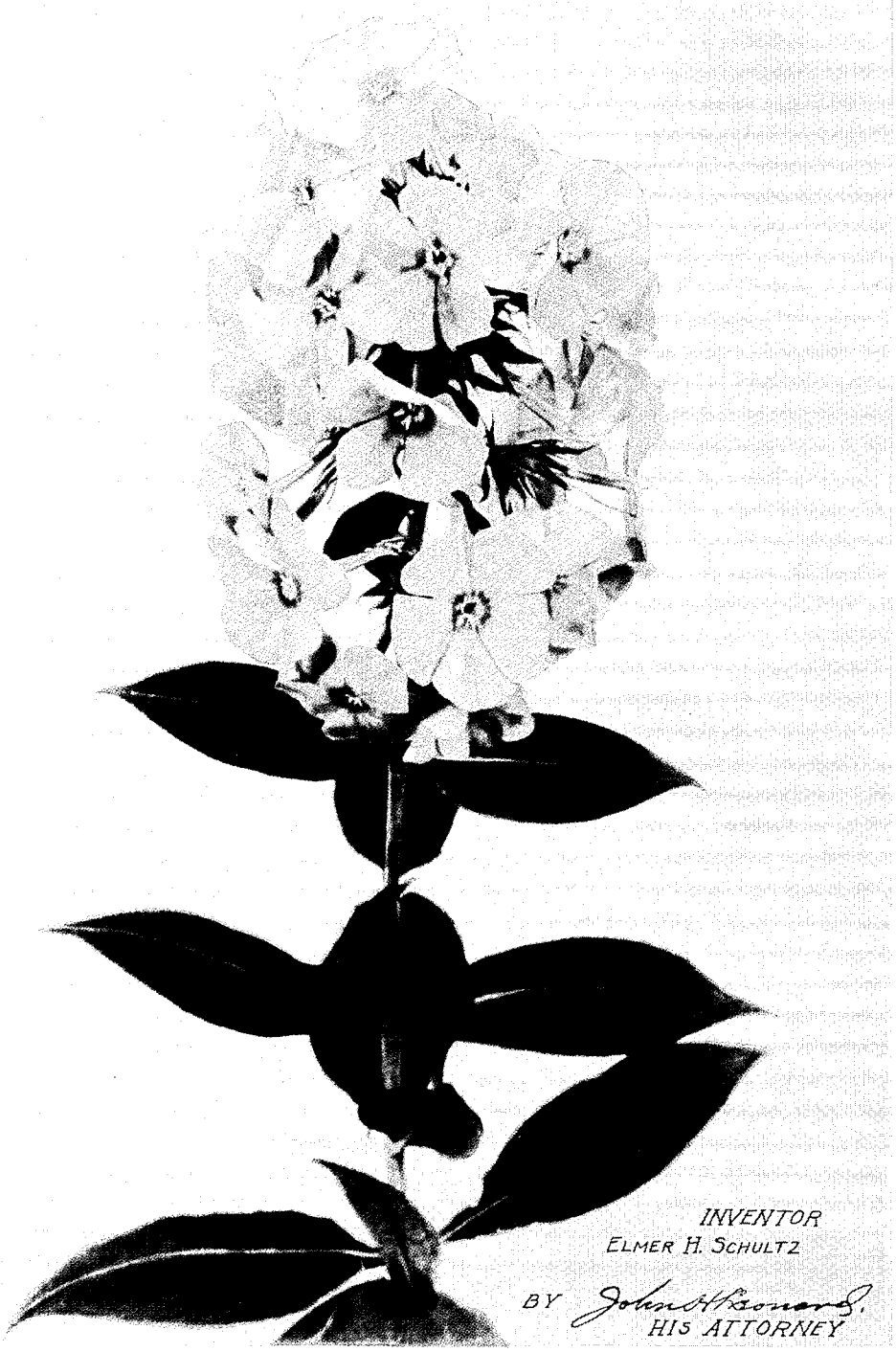
INVENTOR
ELMER H. SCHULTZ
BY John H. Leonard
HIS ATTORNEY Patented June 22, 1937

Plant Pat. 252

UNITED STATES PATENT OFFICE

252

PHLOX

Elmer H. Schultz, Mentor, Ohio, assignor to The Wayside Gardens Company, Mentor, Ohio, a corporation of Ohio Application December 11, 1936, Serial No. 115,430

1 Claim. (Cl. 47—60)

This invention relates to a novel and distinct variety of phlox, the basic variety or genus being that of the paniculata.

The new variety of phlox has a distinctive new color of flower produced by the combination of several shades of red merging into each other, resulting in an objective floret color of an outstandingly bright and sparkling cherry-red color, having a beautiful clear tone, corresponding about to Plate No. 2 J–3, of Maerz and Paul, with a deeper red or maroon center, corresponding about to Plate No. 7 J–4, of Maerz and Paul, and having superimposed the yellow stamens. The flower head presents a glamorous pyramid of cherry-red color, which is made more conspicuous and beautiful by the deeper red or maroon coloring of the floret centers. The flower heads are large and well-shaped and the florets are of good size, measuring about 1¼ to 1½ inches in diameter.

The plant, of medium height, has a very sturdy peduncle because of its thick and heavy stem. The dark green, leathery foliage is prolific from the bloom head to the ground, the color having a bronzy green cast, corresponding about to Plate No. 23 A–12, of Maerz and Paul, and composed of leaves which are glabrous and having prominent aerolate veins. A large number of secondary bloom heads or laterals develop below the main head. The corolla, being surrounded by dark green sepals, has a slight tracing of fiery-orange at the tips of the opening florets, which adds materially to the en masse coloring of the flower. The plant has further a free branching characteristic in growth, with the long lateral reddish green stems carrying the florets.

The permanency of color under adverse weather conditions, such as long periods of hot weather or extensive fall rains, and the texture of the petals, along with an abundance of laterals, provides a continuance of flower color during the entire blooming season, which is a marked improvement over the common varieties.

The common varieties of phlox are subject to attack by insects, the most common being the red spider, and the disease of rust, both of which are destructive of the foliage. An important characteristic of the new type of phlox, is its rust-resisting quality and immunity against attack by insects.

The new phlox was produced by a cross pollinization of the "Columbia" and "Beacon" varieties of phlox. A large number of plants have been reproduced asexually by cuttings from the original seedling of pollinization. A reproduction from seeds produces plants having entirely different characteristics and colors from the applicant's variety, wherefore the plant herein shown, described and claimed can be reproduced only asexually.

The drawing submitted is a colored photograph which approximates as closely as physically possible the actual distinctive and vivid coloring of the new variety. The abundance of laterals provides continuous blooming, and along with the preservative and resistive character of the flower petals and foliage, the plant is very useful for decorative coloring.

Having now described my new phlox and the method of reproducing the same, what I claim is:

A phlox, as herein shown and described, characterized and distinguished by a vivid, sparkling, cherry-red color of bloom, a dark green, leathery foliage having a bronzy green cast, and the flower color substantially withstanding extreme conditions of seasons.

ELMER H. SCHULTZ.